(12) United States Patent
Moody et al.

(10) Patent No.: US 7,476,709 B2
(45) Date of Patent: Jan. 13, 2009

(54) PROCESS FOR PREPARING OLIGONUCLEOTIDES

(75) Inventors: David John Moody, Grangemouth (GB); Donald Alfred Wellings, Manchester (GB); Paul McCormac, Grangemouth (GB)

(73) Assignee: Avecia Biotechnology Inc., Milford, MA (US)

( * ) Notice: Subject to any disclaimer, the term of this patent is extended or adjusted under 35 U.S.C. 154(b) by 581 days.

(21) Appl. No.: 10/512,138

(22) PCT Filed: Apr. 25, 2003

(86) PCT No.: PCT/GB03/01795

§ 371 (c)(1),
(2), (4) Date: Jun. 14, 2005

(87) PCT Pub. No.: WO03/091267

PCT Pub. Date: Nov. 6, 2003

(65) Prior Publication Data

US 2006/0036028 A1    Feb. 16, 2006

(30) Foreign Application Priority Data

Apr. 26, 2002 (GB) ................... 0209539.6

(51) Int. Cl.
*C08F 16/12*   (2006.01)
*C08F 8/12*    (2006.01)
(52) U.S. Cl. .................. 525/118; 525/327.3; 525/328.9
(58) Field of Classification Search ................ 525/118, 525/327.3, 328.9
See application file for complete search history.

(56) References Cited

U.S. PATENT DOCUMENTS

| | | | |
|---|---|---|---|
| 4,908,405 A | 3/1990 | Bayer et al. | 525/61 |
| 5,466,758 A | 11/1995 | Yoon-Sik et al. | 525/386 |
| 5,696,248 A | 12/1997 | Peyman et al. | |
| 5,869,696 A | 2/1999 | Reddy et al. | |
| 6,096,881 A | 8/2000 | Han et al. | 536/25.3 |
| 6,395,842 B1 | 5/2002 | Main | 525/384 |
| 6,506,894 B1 | 1/2003 | Reese et al. | 536/25.3 |
| 6,642,373 B2 | 11/2003 | Manoharan et al. | 536/25.34 |
| 7,365,132 B2 | 4/2008 | Moody et al. | 525/328.9 |

FOREIGN PATENT DOCUMENTS

| | | |
|---|---|---|
| WO | WO 97/27226 | 7/1997 |
| WO | WO 99/09041 | 2/1999 |
| WO | WO 99/62922 | 12/1999 |
| WO | WO 00/02953 | 1/2000 |
| WO | WO 01/26692 | 4/2001 |
| WO | WO 03/045969 | 6/2003 |

OTHER PUBLICATIONS

Balakrishnan et al., "Particle Size Control in Suspension Copolymerization of Styrene, Chloromethylstyrene, and Divinylbenzene", Journal of Applied Polymer Science, 27:135-138 (1982).
Beaucage et al., "The Synthesis of Modified Oligonucleotides by the Phosphoramidite Approach and Their Applications", Tetrahedron Report No. 335, 49:6123-6195 (1993).
Harris, J.M., "Laboratory synthesis of polyethylene glycol derivatives", Journal of Macromolecular Science-Reviews in Macromolecular Chemistry, vol. C-25, No. 3, pp. 325-373 (Jan. 1, 1985).
Hiratani et al., "Preparation and Catalytic Behaviour of Polymers with Pendant Oligoethyleneoxy-groups (Polymers of Non-cyclic Crown Ethers)", Israel Journal of Chemistry, 18:208-213 (1979).
Seliger H. et al.: "Polymer-Supported Nucleic Acid Fragments" Reactive and Functional Polymers, vol. 43, No. 3, 2000, pp. 325-339.

*Primary Examiner*—Randy Gulakowski
*Assistant Examiner*—Olga Asinovsky
(74) *Attorney, Agent, or Firm*—Morgan Lewis & Bockius LLP

(57) ABSTRACT

A process for the preparation of an oligonucleotide is provided. The process comprises the assembly of an oligonucleotide attached to a solid support, wherein the solid support is prepared by a process comprising polymerisation of a monomer which comprises a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid-labile protecting group, preferably an optionally substituted trityl group.

15 Claims, No Drawings

PROCESS FOR PREPARING OLIGONUCLEOTIDES

The present invention relates to a process for the preparation of oligonucleotides, and to compounds for use therein.

PCT/GB99/02193 discloses a series of novel polymer resin supports which find use as supports in solid phase organic synthesis (SPOS).

We have found that polymers prepared by a particular process are especially suited to the preparation of oligonucleotides.

According to a first aspect of the present invention there is provided a process for the preparation of an oligonucleotide which comprises the assembly of an oligonucleotide attached to a solid support, wherein the solid support is prepared by a process comprising polymerisation of a monomer which comprises a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid-labile protecting group, preferably an optionally substituted trityl group.

The hydroxypoly$C_{2-4}$alkyleneoxy chains attached to the monomer according to the present invention are often selected from hydroxypolyethyleneoxy (HO(CH$_2$CH$_2$O)$_{2-10}$—), hydroxypolypropyleneoxy (HO(CH$_2$CH(CH$_3$)O)$_{2-10}$—) and hydroxypolybutyleneoxy (HO(CH$_2$CH(C$_2$H$_5$)O)$_{2-10}$—) chains. In a preferred embodiment of the invention the hydroxypoly$C_{2-4}$alkyleneoxy chain is hydroxypolyethyleneoxy.

The number of $C_{2-4}$alkyleneoxy groups in the hydroxypoly$C_{2-4}$alkyleneoxy chain can range from 2 to 10, but is preferably from 2 to 8 and more preferably from 3 to 5. Most preferably, there are four $C_{2-4}$alkyleneoxy groups in the hydroxypoly$C_{2-4}$alkyleneoxy chain.

In a highly preferred embodiment of the invention the hydroxypoly$C_{2-4}$alkyleneoxy chain is hydroxytetraethyleneoxy (HO(CH$_2$CH$_2$O)$_4$—).

The polymerisable unit of the monomer according to the present invention is often selected from optionally substituted styrenes, acrylates and acrylamides. In a preferred embodiment of the invention the polymerisable unit is an optionally substituted styrene, optionally substituted methylstyrene, optionally substituted ethyl (meth)acrylate, optionally substituted propyl (meth)acrylate or optionally substituted N-methyl (meth)acrylamide.

In a highly preferred embodiment of the invention the polymerisable unit is an optionally substituted styrene or optionally substituted methylstyrene.

Where the polymerisable unit is an optionally substituted styrene or optionally substituted methylstyrene, the phenyl ring of the styrene is preferably optionally substituted by 1 or 2 substituents often selected from methyl, ethyl, propyl, fluoro, chloro and bromo.

When the polymerisable unit is an optionally substituted styrene or optionally substituted methylstyrene, preferably the protected hydroxypoly$C_{2-4}$ alkyleneoxy chain is attached to an optionally substituted styrene or optionally substituted methylstyrene via a phenoxy ether linkage, ie an oxygen atom directly attached to the phenyl ring of the optionally substituted styrene or optionally substituted methylstyrene.

Acid labile protecting groups are groups which are labile under acid conditions. Acid labile protecting groups include poly-aryl methane protecting groups.

Poly-aryl methane protecting groups include optionally substituted di-aryl methanes and optionally substituted tri-aryl methanes. Optional substituents may reside on one or more of the aryl groups, and each aryl group may carry one or more substituents. Di-aryl methanes may also be optionally substituted on the carbon to which the two aryls are attached, preferably the optional substituent is an alkyl group.

Aryl refers to aryl groups which may contain 1 ring or 2 or more fused rings, the fused rings optionally may include cycloalkyl, aryl or heterocyclic rings. Examples of aryl groups include phenyl, tolyl, fluorophenyl, chlorophenyl, bromophenyl, trifluoromethylphenyl, anisyl, naphthyl xanthyl, pyridyl, pyrimidyl, thiophenyl, furanyl, indolyl, quinolyl and isoquinolyl groups.

Preferred aryl groups are optionally substituted phenyl, optionally substituted naphthyl, and optionally substituted xanthyl groups.

Alkyl groups which may substitute the carbon of a di-aryl methane include linear and branched alkyl groups comprising up to 20 carbon atoms, particularly from 1 to 7 carbon atoms, preferably from 1 to 5 carbon atoms, most preferably 1 or 2 carbon atoms. Examples include methyl, ethyl, propyl, and iso-propyl groups.

When the poly-aryl methane is substituted, the substituent(s) should be such so as not to adversely affect the stability of the protecting group or the ability to remove the protecting group under acid conditions. Optional substituents include halogen, cyano, nitro, hydrocarbyl, amino, thiol, acyl, hydrocarbyl, perhalogentated hydrocarbyl, heterocyclyl, hydrocarbyloxy, poly(oxyalkylene)oxy, mono or di-hydrocarbylamino, hydrocarbylthio, esters, carbonates, amides, sulphonyl and sulphonamido groups wherein the hydrocarbyl groups are generally alkyl or aryl groups as defined above. One or more substituents may be present.

Examples of poly-aryl methane protecting groups include diphenylmethyl, naphthyldiphenylmethyl, phenylxanthyl [pixyl], triphenylmethyl [trityl], di-methoxyphenylphenylmethyl [dimethoxy trityl], methoxyphenyl-di-phenylmethyl [monomethoxy trityl], and 2-chlorophenyidi-phenylmethyl [2-chlorotrityl] groups.

Optionally substituted trityl groups include triphenylmethyl [trityl], di-methoxyphenylphenylmethyl [dimethoxy trityl], methoxyphenyl-di-phenylmethyl [monomethoxy trityl], and 2-chlorophenyldi-phenylmethyl [2-chlorotrityl] groups.

In a preferred embodiment of the invention, the monomer is a compound of formula (1)

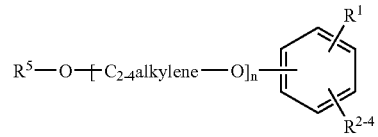

wherein
$R^1$ is an optionally substituted ethylene group;
$R^{2-4}$ are independently hydrogen, hydrocarbyl, halogen, or hydrocarbyloxy;
$R^5$ is an acid labile protecting group; and
n is 2 to 10.

Preferably, the acid labile protecting group is a poly-aryl methane protecting group. More preferably $R^5$ is a poly-aryl methane protecting group of formula:

—CR$^6$R$^7$R$^8$ wherein:
$R^6$ is hydrogen, optionally substituted alkyl or optionally substituted aryl group; and $R^7$ and $R^8$ are each independently optionally substituted aryl groups, or $R^7$ & $R^8$ are optionally substituted aryl groups which may be linked to form an optionally substituted ring.

Alkyl groups which may be represented by $R^6$ include linear and branched alkyl groups comprising up to 20 carbon atoms, particularly from 1 to 7 carbon atoms, preferably from 1 to 5 carbon atoms, most preferably 1 or 2 carbon atoms. Examples include methyl, ethyl, propyl and isopropyl groups.

Aryl groups which may be represented by $R^6$, $R^7$ and $R^8$ may contain 1 ring or 2 or more fused rings, the fused rings optionally may include cycloalkyl, aryl or heterocyclic rings. Examples of aryl groups include phenyl, tolyl, fluorophenyl, chlorophenyl, bromophenyl, trifluoromethylphenyl, anisyl, naphthyl, pyridyl, pyrimidyl, thiophenyl, furanyl, indolyl, quinolyl and isoquinolyl groups.

Preferred aryl groups are optionally substituted phenyl.

When $R^7$ & $R^8$ are optionally substituted aryl groups which are linked in such a way that when taken together with the carbon atom to which they are attached that a ring is formed, it is preferred that the ring is a 5, 6 or 7 membered ring. Examples where $R^7$ & $R^8$ are optionally substituted aryl groups which are linked to form an optionally substituted ring include xanthyl groups.

When any of $R^6$, $R^7$ or $R^8$ is a substituted alkyl or substituted aryl group, the substituent(s) should be such so as not to adversely affect the stability of the protecting group or the ability to remove the protecting group under acid conditions. Optional substituents include halogen, cyano, nitro, hydrocarbyl, amino, thiol, acyl, hydrocarbyl, perhalogentated hydrocarbyl, heterocyclyl, hydrocarbyloxy, poly(oxyalkylene)oxy, mono or di-hydrocarbylamino, hydrocarbylthio, esters, carbonates, amides, sulphonyl and sulphonamido groups wherein the hydrocarbyl groups are generally alkyl, aryl, alkaryl and aralkyl groups, the alkyl and aryl groups are as defined above. One or more substituents may be present.

Most preferably, $R^5$ is a poly-aryl methane protecting group of formula:

—$CR^6R^7R^8$ wherein:

$R^6$ is an optionally substituted aryl group; and $R^7$ and $R^8$ are each independently optionally substituted aryl groups, or $R^7$ & $R^8$ are optionally substituted aryl groups which may be linked to form an optionally substituted ring.

In a highly preferred embodiment of the present invention, the acid labile protecting group is an optionally substituted trityl group.

In a most preferred embodiment of the invention, the monomer is a compound of formula (1a)

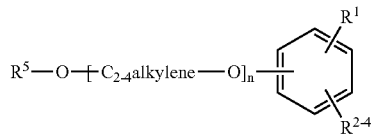

wherein $R^1$ is an optionally substituted ethylene group;

$R^{2-4}$ are independently hydrogen, hydrocarbyl, halogen, or hydrocarbyloxy;

$R^5$ is an optionally substituted trityl group; and n is 2 to 10.

Preferably, $R^1$ is a $CH=CH_2$, $CH=CHCH_3$, or $C(CH_3)=CH_2$ group. Most preferably, $R^1$ is a $CH=CH_2$.

Preferably, the $R^5O$—[—$C_{2-4}$alkylene-O—]$_n$ group is para to $R^1$.

Preferably, [—$C_{2-4}$alkylene-O—]$_n$ is [—$CH_2CH_2O$—]$_n$, [—$CH_2CH(CH_3)O$—]$_n$ or [—$CH_2CH(C_2H_5)O$—]$_n$ and most preferably [—$CH_2CH_2O$—]$_n$.

Preferably n is 2 to 8, more preferably n is 3 to 5. Most preferably n is 4.

Preferably $R^{2-4}$ are all hydrogen.

Hydrocarbyl includes alkyl, aryl, alkaryl and aralkyl groups. Preferably when any of $R^{2-4}$ are hydrocarbyl or hydrocarbyloxy groups the hydrocarbyl is an alkyl group, most preferably a $C_{1-4}$ alkyl group.

Optionally, in the process of the present invention the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an optionally substituted trityl group may comprise a mixture of isomers.

Preferably, when a mixture of isomers is used in the process of the present invention, the monomer is a compound of formula (1) or (1a). Most preferably, the monomer is a mixture of isomers wherein $R^5O$—[—$C_{2-4}$alkylene-O—]$_n$ group and $R^1$ occupy isomeric positions on the phenyl ring.

The monomers are polymerised, preferably under conditions to produce cross-linking to form solid supports suitable for use in the preparation of oligonucleotides.

Preferably the monomer comprising a protected hydroxypoly$C_{2-4}$ alkyleneoxy chain attached to a polymerisable unit is co-polymerised in the presence of a cross linking monomer.

The extent of cross linking in the polymers may be determined by the concentration of cross linking monomer in the polymerisation reaction. Generally the weight % of cross-linking monomer is in the range of from 0.1 to 70%, commonly from 0.5 to 20%, such as from 1 to 10%, and most preferably no more than 5% by weight. Polymers comprising no more than 20% by weight of cross-linking monomer are generally swellable, whilst polymers comprising greater than 20% of crosslinking monomer are generally not swellable.

Suitable cross-linking monomers include divinyl benzene (DVB) or multifunctional (meth)acrylates such as di/tri acrylates or di/tri methacrylates such as ethylene glycol diacrylate, ethylene glycol dimethacrylate, trimethylopropane trimethacrylate, trivinylbenzene or N,N'-bis-acryloyl ethylene diamine. Preferably, the cross-linking monomer is DVB.

Preferably 0.5 to 5% by weight of DVB is used. Most preferably 1 to 3% by weight DVB is used.

In certain aspects of the present invention a level of at least 5% crosslinking monomer may be used in conjunction with compounds miscible with the organic phase which can act as pore-forming agents or porogens. Typical porogens can include, but are not limited to, organic compounds which are good solvents for the polymer, such as organic aromatic hydrocarbons, chlorinated aliphatic or aromatic hydrocarbons and cyclic aliphatic ethers, organic compounds which are poor solvents for the resulting polymer, such as aliphatic alcohols, ketones, aliphatic hydrocarbons, aliphatic carboxylic acids and linear polymers. Preferably porogens are selected from toluene, xylene, chlorobenzene, tetrahydrofuran, dioxane, 2-ethyl-1-hexanol, 2-octanol, 1-decanol, 1-dodecanol, acetone, butanone, n-heptane, n-decane, 1-decanoic acid and linear polystyrene of molecular weight 500 to 5000000 g/mol. The resulting polymers have substantially non-swelling behaviour and generally possess a meso- to macro-porous nature, by which mode reagents can access the polymer-bound functionality.

Optionally, in the process of the present invention, the monomer comprising a protected hydroxypoly$C_{2-4}$alkyleneoxy chain attached to a polymerisable unit is co-polymerised in the presence of one or more co-monomers selected from styrenes, for example styrene, hydroxystyrene, methoxystyrene, methylstyrene, hydroxymethylstyrene and chloromethylstyrene, esters of acrylic acid and esters of (meth) acrylic acid, for example methyl acrylate, ethyl acrylate, methyl methacrylate, ethyl acrylate, hydroxyethyl (meth) acrylate and hydroxypropyl (meth)acrylate, and acrylamides, for example N-methyl acrylamide and N-methylol (meth) acrylamide; wherein the phenyl ring in the styrenes is optionally substituted by 1 or 2 substituents often selected from methyl, ethyl, propyl, fluoro, chloro and bromo and wherein hydroxy groups, especially phenolic hydroxy groups, which may be present in the co-monomers are optionally protected and may subsequently be deprotected. It is preferred that any co-monomer employed is free from protected or unprotected hydroxy groups.

In a preferred polymerisation, the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an optionally substituted trityl group is co-polymerised in the presence of one or more cross linking monomers, and one or more monomers selected from styrenes, esters of acrylic acid and esters of (meth)acrylic acid, or acrylamides.

In a highly preferred polymerisation, the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkylenebxy groups and wherein the hydroxypoly$C_{2-4}$ alkyleneoxy chain is protected with an optionally substituted trityl group is co-polymerised in the presence of DVB and styrene.

When the solid support is produced by polymerisation of a mixture of monomers comprising the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$alkyleneoxy groups and wherein the hydroxypoly$C_{2-4}$ alkyleneoxy chain is protected with an acid labile protecting group, preferably an optionally substituted trityl group, and one or more monomers selected from styrenes, esters of acrylic acid and esters of (meth)acrylic acid, or acrylamides, the weight percentage of the monomer comprising a protected hydroxypoly$C_{2-4}$alkyleneoxy chain attached to a polymerisable unit of the total weight of the monomers present is preferably in the range of from 1-99%, more preferably in the range of from 5-80% and most preferably from 15% to 70%.

The process of the present invention is preferably carried out by aqueous suspension polymerisation. The monomers are suspended as droplets (1-1000 μm) in water. Stabilisers are usually added to prevent agglomeration of the droplets, for example polyvinyl alcohol, polyacrylic acid, polyvinyl pyrrolidone, polyalkylene oxide, derivatives of cellulose, such as hydroxypropylmethylcellulose or ethylcellulose, barium sulphate, magnesium sulphate or sodium sulphate. The suspension is also normally stirred to maintain the suspension.

Optionally, organic non-water miscible solvents may be used in the polymerisation process. Organic non-water miscible solvents may assist droplet formation in aqueous suspension polymerisation, or may act as porogens.

Optionally inorganic salts may be added to the aqueous phase in aqueous suspension polymerisation. Inorganic salts may assist droplet formation by suppressing monomer solubility in the aqueous medium.

A free radical initiator is preferably used to initiate polymerisation. The type of initiator will generally be selected based on the monomers used. Examples of preferred free radical initiators include benzoyl peroxide, dioctanoyl peroxide, lauroyl peroxide, 2,2'-azobisisobutyronitrile and 2,2'-azobis(2,4-dimethylvaleronitrile).

Polymerisation is typically assisted by heating the mixture in the range of 15° C. to 160° C., preferably 50° C. to 90° C. It will be recognised that the temperature to which the mixture can be heated depends upon the type of monomer and initiator employed.

The resultant polymer may then be washed with suitable solvents such as tetrahydrofuran, methanol and water, dried and bead size classified, for example, by sieving.

For use in the preparation of oligonucleotides, the acid labile protecting group is removed from solid support by methods known in the art for the removable of the given protecting group to give the cross-linked polymer containing free hydroxy groups. Appropriate methods, particularly for removal of optionally substituted trityl groups include, for example, acid hydrolysis. Commonly a mixture of an optionally substituted acetic acid, such as dichloro or trifluoroacetic acid in a solvent, such as methylene chloride or toluene can be employed. The reader is referred to Advanced Organic Chemistry, $4^{th}$ Edition, by Jerry March, published by John Wiley & Sons 1992, for general guidance on reaction conditions and reagents. Where appropriate, other methods may be also used for the removal of the acid labile protecting groups, for example the use of iodine under neutral conditions may be used to remove trityl groups, and photolysis may be used to remove pixyl groups.

Cross-linked polymers containing a free hydroxy group are usually produced as beads which range in size from 10 μm to 2000 μm. Preferably the bead size is from 50 μm to 1000 μm and most preferably from 75 μm to 500 μm. The cross-linked polymer beads are generally produced by an aqueous suspension polymerisation process, for example see Journal of Applied Polymer Science, 1982, 27, 133-138, incorporated herein by reference.

The polymer support obtained when the protecting groups are removed from the support preferably has a hydroxy functionality of from 0.1 to about 5, for example up to 4.8 meq (milliequivalents) of hydroxy per gram of polymer, and often from 0.5 to 3.5, commonly 1.0 to 3.3 meq per gram for example from 1.5 to 3 meq per gram of polymer. In many embodiments, the polymer support obtained when the protecting groups are removed have from 0.5 to 2 meq of hydroxy per gram of polymer.

The oligonucleotide synthesis can take place by direct attachment to the functional group of the solid support. However, in many embodiments, it is preferred to employ a cleavable linker to attach the oligonucleotide to the solid support via the functional group. Examples of such linkers are well known in the art and include particularly succinyl, oxaloyl and trityl linkers.

Oligonucleotides that can be prepared by the process of the present invention include oligodeoxyribonucleotides, oligoribonucleotides, and oligonucleotides comprising mixtures of deoxyribo- and ribonucleosides. The oligonucleotides may be modified by one or more modifications known in the field of oligonucleotide chemistry, for example ribonucleoside moieties may be modified at one or more of the 2'-positions by the presence of 2'-alkoxy group, such as a methoxy or methoxyethoxy group. Deoxyribonucleosides moieties may be modified at the 2'-position by the presence of a substituent, such as a halo group, especially a fluoro group, or by an alkenyl group such as an allyl group. A basic nucleoside moieties may also be present. One or more locked nucleoside may be present. In many embodiments, the oligonucleotides will be in the form of the natural D-isomer. However, some or all of the oligonucleotide may represent an unnatural isomer, for example an L-isomer or a B-anomer, either in whole or in part. The internucleoside linkages may be natural phosphate, or one or more modified linkages, for example phosphorothioate or phosphoramidate linkages may be present. Fully phosphorothioated or fully phosphoramidated oligonucleotides may be prepared.

The oligonucleotide may comprise one or more protecting groups. Examples of such protecting groups, and the positions which they can be employed to protect, are well known to those skilled in the art, and include trityl, monomethoxytrityl and dimethoxytrityl groups, levulinoyl groups, isobutyryl groups, benzoyl groups, silyl groups, such as trialkylsilyl groups, for example t-butyldimethylsilyl groups, acetyl groups and carbonate groups, such as BOC and especially FMOC.

The oligonucleotides may comprise natural and/or unnatural nucleobases including adenine, guanine, cytosine, thymine, uracil, 7-deazaguanine, 7-deaza-8-azaguanine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo4-methylthio-5-methylpyrimidine, 2-thiocarbonyl4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

The oligonucleotides may be prepared by methods known in the art for the assembly of oligonucleotides on a solid support. In many such approaches, a reactive phosphorus-containing group is coupled with a reactive site on a nascent oligonucleoide to form an internucleotide phosphorus linkage. Examples of suitable methods include the phosphotriester approach, the H-phosphonate approach, and particularly the phosphoramidite approach. The nascent oligonucleotide commonly initially comprises a nucleoside, or nucleoside analogue, which has been attached to a solid support, preferably via a cleavable linker. In many embodiments, the nascent oligonucleotide comprises a deoxyribonucleoside or ribonucleoside, most preferably attached via the 3' position to the solid support. Other methods of attachment to the solid support are known in the art, and are applicable in the present invention, and include for example attachment via a nucleobase, and attachment via the 2'- or 5'-position of ribo- and deoxyribonucleosides. The reactive site may comprise a free amino or thiol moiety, but is preferably a free hydroxy group. The nascent oligonucleotide may be attached to the solid support with the reactive site protected by a suitable protecting group. The protecting group is therefore removed prior to assembly of the oligonucleotide. It is most preferred that the reactive site is the 5'-position of a deoxyribonucleoside or ribonucleoside.

When the phosphotriester approach is employed, typically, an activated protected nucleoside or oligonucleotide phosphate ester is reacted with an alcohol to form an internucleotide phosphodiester linkage. Activators for use in the phosphotriester approach are well known in the art, and include acid chlorides, including for example sulfonyl chlorides.

When the H-phosphonate approach is employed, typically, a protected nucleoside or oligonucleotide H-phosphonate monoester is coupled with a nascent oligonucleotide comprising a free hydroxy group to form a protected oligonucleotide H-phosphonate diester. The coupling preferably takes place in the presence of a coupling agent. The protected oligonucleotide H-phosphonate diester may be deprotected to form a nascent oligonucleotide comprising a free hydroxy group, which can then be further coupled with a nucleoside or oligonucleotide H-phosphonate monoester. The process can be repeated as often as necessary until the desired sequence is assembled. On completion of assembly of the desired sequence, the H-phosphonate diester linkages may be oxidised or sulfurised to form a phosphate or phosphorothioate oligonucleotide. Alternatively, oxidation or sulfurisation may be carried out after each coupling. Coupling agents and sulfurisation agents suitable for use in the H-phosphonate approach are well known in the art, and include those disclosed in WO99/09041 and International application PCT/GB02/005177, incorporated herein by reference.

The preferred reactive phosphorus-containing group is the phosphoramidite group. Nucleoside phosphoramidites are advantageously coupled with free hydroxy groups on the nascent oligonucleotide, preferably coupling a 3'-nuclesode phosphoramidite with a free 5'-nucleoside hydroxy group. The oligonucleotide is preferably prepared by coupling a deoxyribonucleside-3'-phosphoramidite or ribonucleoside-3'-phosphoramidite with a nascent oligonucleotide comprising a free 5'-hydroxy group. However, it will be recognised that the process according to the present invention is equally applicable to the coupling of a 5'-phosphoramidite to a free 3'-hydroxy group.

Preferred phosphoramidites are compounds of formula:

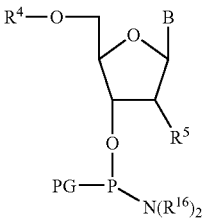

wherein $R^4$ is a protecting group, preferably a trityl, monomethoxytrityl or dimethoxytrityl group, B is a nucleoside base, $R^5$ represents —H, —F —$OR^6$, —$NR^7R^8$, —$SR^9$, or a substituted or unsubstituted aliphatic group, such as methyl or allyl. PG is a phosphorus protecting group, commonly a cleavable phosphorus protecting group employed in oligonucleotide synthesis, and preferably a substituted or unsubstituted aliphatic group or a group of formula —$OCH_2CH_2CN$, —$SCH_2CH_2CN$, —$OR^{11}$, —$SR^{11}$, —O—$CH_2CH_2$—$Si(CH_3)_2C_6H_5$, —O—$CH_2CH_2$—$S(O)_2$—$CH_2CH_3$, —O—$CH_2CH_2$—$C_6H_4$—$NO_2$, —S—$CH_2CH_2$—$Si(CH_3)_2C_6H_5$, —S—$CH_2CH_2$—$S(O)_2$—$CH_2CH_3$, or —S—$CH_2CH_2$—$C_6H_4$—$NO_2$. $R^6$ represents —H, a substituted or unsubstituted aliphatic group (e.g., methyl, ethyl, methoxyethyl or allyl), a substituted or unsubstituted aryl group, a substituted or unsubstituted aralkyl, an alcohol protecting group, especially a base-labile or a silyl protecting group, or —$(CH_2)_q$—$NR^{12}R^{13}$. $R^7$ and $R^8$ are each, independently, —H, a substituted or unsubstituted aliphatic group, or an amine protecting group. Alternatively, $R^7$ and $R^8$ taken together with the nitrogen to which they are attached form a heterocyclyl group. $R^9$ represents —H, a substituted or unsubstituted aliphatic group, or a thiol protecting group. $R^{11}$ represents a substituted or unsubstituted aliphatic group, a substituted or unsubstituted aryl group or a substituted or unsubstituted aralkyl group. $R^{12}$ and $R^{13}$ are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group. Alternatively, $R^{12}$ and $R^{13}$ taken together with the nitrogen to which they are attached form a heterocyclyl group. q is an integer from 1 to about 6. Each $R^{16}$ independently is a $C_{1-6}$ alkyl group, preferably an isopropyl group, or the group $N(R^{16})_2$ represents a heterocyclic group. The phosphoramidite employed is commonly a betacyanoethyloxy-N,N-diisopropyl phosphoramidite.

Amine, alcohol and thiol protecting groups which may be present in the preferred phosphoramidites are well known to those skilled in the art. For examples of amine protecting groups see Greene, et al., *Protective Groups in Organic Synthesis* (1991), John Wiley & Sons, Inc., pages 309-405, the teachings of which are incorporated herein by reference in their entirety. Preferably, amines are protected as amides or carbamates. For examples of hydroxy protecting groups see Id., pages 10-142, the teachings of which are incorporated herein by reference in their entirety. For examples of thiol protecting groups see Id., pages 277-308, the teachings of which are incorporated herein by reference in their entirety. Protecting groups which may be present other then those represented by $R^4$ are preferably selected to be orthogonal to the protecting groups represented by $R^4$.

Activators which can be employed in the process of the present invention are well known in the field of oligonucleotide synthesis. Examples of suitable activators include tetrazole, substituted tetrazole derivatives, such as S-ethyl tetrazole and S-phenyl tetrazole, and substituted imidazole derivatives such as dicyanoimidazole.

Preferred activators include salts of heteroaromatic compounds comprising fewer than four nitrogen atoms in the heteroaromatic ring, especially heteroaromatic compounds comprising a 5 or 6 membered ring which comprises one or two nitrogen atoms. Examples include pyridinium, imidazolinium and benzimidazolinium salts, particularly the hexafluorophosphate, tetrafluoroborate, triflate, hydrochloride, trifluoroacetate, dichloroacetate, O-mesyl, O-tosyl, bromide or trifluorosulphonyl salts as disclosed in PCT application WO 99/62922 (incorporated herein by reference); benzotriazole and derivatives thereof, especially hydroxybenzotriazole; and saccharin or a saccharin derivative, preferably employed as a salt-complex formed with an organic base, especially the N-methylimidazole, pyridine or 3-methylpyridine salts of saccharin.

The saccharin or saccharin derivative which can be employed preferably has the general formula:

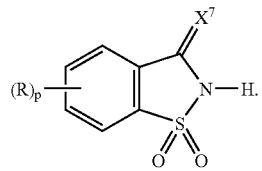

I

In Formula I, p is 0 or an integer from 1 to 4. R for each occurrence is a substituent, preferably each independently, a halo, a substituted or unsubstituted aliphatic group, —$NR^1R^2$, —$OR^3$, —$OC(O)R^3$, —$C(O)OR^3$, cyano, a substituted or unsubstituted aryl, a substituted or unsubstituted heterocyclyl, —CHO, —$COR^3$, —$NHCOR^3$, a substituted or unsubstituted aralkyl, halogenated alkyl (e.g., trifluoromethyl and trichloromethyl), or —$SR^3$. Preferably, R is halo, a substituted or unsubsbtuted aliphatic group, —$NR^1R^2$, —$OR^3$, —$OC(O)R^3$, —$C(O)OR^3$, or cyano. Alternatively, two adjacent R groups taken together with the carbon atoms to which they are attached form a six membered saturated or unsaturated ring. Preferably, the six membered ring formed is an aromatic ring. $R^1$ and $R^2$ are each, independently, —H, a substituted or unsubstituted aliphatic group, a substituted or unsubstituted aryl group, a substituted or unsubstituted aralkyl group; or together with the nitrogen to which they are attached form a heterocyclyl group. $R^3$ is a substituted or unsubstituted aliphatic group, a substituted or unsubstituted aryl group, or a substituted or unsubstituted aralkyl group. X is O or S. Preferably, X is O. It is particularly preferred that X is O and p is 0.

Suitable substituents which may be present include aryl groups, halogenated aryl groups, alkyl groups, halogenated alkyl (e.g. trifluoromethyl and trichloromethyl), aliphatic ethers, aromatic ethers, benzyl, substituted benzyl, halogens, particularly chloro and fluoro groups, cyano, nitro, —S-(aliphatic or substituted aliphatic group), and —S-(aromatic or substituted aromatic) groups.

Preferably the saccharin or saccharin derivative is employed as a salt complex with an organic base.

Organic bases which can form salt-complexes with saccharin or saccharin derivatives are organic compounds that have a tendency to accept protons at pH 7. Preferred organic bases are secondary amines, tertiary amines or azaheterocyclyl bases, each of which may be substituted or unsubstituted by one or more substituents. An aprotic organic base is an organic base that has no hydrogen bonding protons in its chemical structure before accepting a proton. Aprotic organic bases such as tertiary amines and aprotic azaheterocyclyl compounds are preferably used in conjunction with compounds of formula 1, as described herein.

Azaheterocyclyl bases, as used herein, include heteroaryl groups which have one or more nitrogen atom in the aromatic ring and heteroalicyclyl groups that have at least one nitrogen atom in the non-aromatic ring system. Preferably, azaheteroaryl bases have five- or six-membered aromatic rings with from one to three nitrogens in the aromatic ring. Preferably, azaheteroalicyclyl compounds are five- or six-membered rings, commonly comprising one or two nitrogens in the ring. Examples of azaheterocyclyl bases include pyrimidines, 1-alkylpyrazoles, especially 1-($C_{1-4}$ alkyl)pyrazoles, 1-arylpyrazoles, 1-benzylpyrazoles, pyrazines, N-alkylpurines, especially N-($C_{1-4}$ alkyl)purines, N-arylpurines, N-benzylpurines, N-alkylpyrroles, especially N-($C_{1-4}$ alkyl) pyrroles, N-arylpyrroles, N-benzylpyrroles, pyridines, N-alkylimidazoles, especially N-($C_{1-4}$ alkyl)imidazoles, N-arylimidazoles, especially N-phenylimidazole, N-benzylimidazoles, quinolines, isoquinolines, quinoxalines, quinazolines, N-alkylindoles, especially N-($C_{1-4}$ alkyl)indoles, N-arylindoles, N-benzylindoles, N-alkylbenzimidazoles especially N-($C_{1-4}$ alkyl)benzimidazoles, N-arylbenzimidazoles, N-benzylbenzimidazoles, triazine, thiazole, 1-alkyl-7-azaindoles, especially 1-($C_{1-4}$ alkyl)-7-azaindoles, 1-aryl-7-azaindoles, 1-benzyl-7-azaindoles, pyrrolidines, morpholines, piperidines, and piperazines. Especially preferred azaheterocyclyl bases are pyridines, such as pyridine and 3-methylpyridine, and N-($C_{1-4}$ alkyl) imidazoles, such as N-methylimidazole.

Tertiary amines are organic bases that have a nitrogen atom which is bonded to three carbon atoms, often to three aryl, commonly phenyl, and/or alkyl groups, commonly to three alkyl groups, including for example trialkylamines such as trimethylamine, triethylamine, and diisopropylethylamine. In addition, tertiary amines can be azaheterocyclyl groups wherein the nitrogen atom is aprotic. Tertiary amines that are azaheterocyclyl groups are preferred. Examples of azaheterocyclyl tertiary amines are N-alkylpyrrolidines, N-arylpyrrolidines, N-alkylpyrroles, N-arylpyrroles, N-alkylmorpholines, N-arylmorpholines, N-alkylpiperidines, N-arylpiperidines, N,N-dialkylpiperazines, N,N-diarylpiperazines, N-alkyl-N-aryl-piperazines, quinuclidines, 1,5-diazabicyclo[4.3.0]non-5-enes and 1,8-diazabicydo[5.4.0]undec-7-enes. Tertiary amines can also be azaheteroaryl or azaheteroalicyclyl compounds.

Secondary amines are organic bases comprising a nitrogen bonded to a single hydrogen and to two carbon atoms. Commonly the nitrogen atom is bonded to two alkyl or aryl groups or forms part of an azaheterocyclic group. Examples of secondary amine compounds include diethylamine and diisopropylamine.

Particularly preferred organic bases include pyridine, 3-methylpyridine, and N-methylimidazole.

The process according to the present invention may employ such process steps as are conventionally carried out for the solid-phase synthesis of oligonucleotides using phosphoramidite chemistry, including sulfurization, oxidation and capping stages.

When a sulfurization agent is employed, preferably the sulfurization agent is an organic sulfurization agent.

Examples of organic sulfurization agents include 3H-benzodithiol-3-one 1,1-dioxide (also called "Beaucage reagent"), dibenzoyl tetrasulfide, phenylacetyl disulfide, N,N,N',N'-tetraethylthiuram disulfide, elemental sulfur, and 3-amino-[1,2,4]-dithiazole-5-thione (see U.S. Pat. No. 6,096,881, the entire teachings of which are incorporated herein by reference).

Typical reaction conditions for sulfurization of an oligonucleotide using the above agents can be found in Beaucage, et al., *Tetrahedron* (1993), 49:6123, which is incorporated herein by reference.

Preferred sulfurization reagents are xanthane hydride, 3-amino-[1,2,4]-dithiazole-5-thione and phenylacetyl disulfide.

Sulfurization of an oligonucleotide may be carried out by, for example use of a solution of 3-amino-[1,2,4]-dithiazole-5-thione in an organic solvent, such pyridine/acetonitrile (1:9) mixture or pyridine, having a concentration of about 0.05 M to about 0.2 M.

Examples of oxidising agents which may be employed include iodine and peroxides, such as t-butylhydroperoxide.

A desired oligonucleotide can be prepared for example by a sequence of steps which comprise coupling a protected, commonly a 5'-protected, nucleoside phosphoramidite with a free hydroxy group, oxidising or sulfurizing the protected phosphite triester formed in the coupling step to form a phosphate or phosphorothioate oligonucleotide, removing the protecting group from the oligonculeotide, and repeating the cycle until the desired sequence has been assembled. The oligonucleotide can be cleaved from the solid support, and any remaining protecting groups, such as nucleobase and phosphorus protecting groups can be removed using conditions known in the art.

The process according to the present invention is preferably carried out in the presence of a solvent which causes the solid support to swell. It will be recognised that the nature of the solvent will be selected based upon the nature of the solid support employed. Examples of suitable solvents are well known in the art, and include in particular acetonitrile, dimethylformamide, N-methylpyrrolidinone, dichloromethane, THF and pyridine.

The process according to the present invention can be carried out in a wide range of appropriate reaction vessels, including, for example, columns, stirred vessels and fixed bed reactors.

The process according to the present invention enables more efficient synthesis of oligonucleotides compared with processes employing alternative hydroxyalkyleneoxy derivatised solid supports.

According to a further aspect of the present invention, there is provided a composition of matter having the formula:

wherein:

Ps represents a polymer obtained by a process comprising polymerisation of a monomer which comprises a protected hydroxypolyC$_{2-4}$ alkyleneoxy chain attached to a polymerisable unit wherein the protected hydroxypolyC$_{2-4}$ alkyleneoxy chain contains from 2 to 10 C$_{2-4}$ alkyleneoxy groups and wherein the hydroxypolyC$_{2-4}$ alkyleneoxy chain is protected with an acid-labile protecting group, preferably an optionally substituted trityl group;

Z represents a single bond or a cleavable linker; and

Q represents H, a protecting group, a nucleoside or an oligonucleotide, provided that Q is not H when Z represents a single bond.

Polymers which can be represented by Ps are as described above.

It will be recognised that when Z represents a cleavable linker, that the cleavable linker bonds to the terminal atom of the poly(alkyleneoxy) chain and similarly that when Z represents a single bond, that the group Q is bonded to the terminal atom of the poly(alkyleneoxy) chain. This atom is most commonly an oxygen atom, although where the polymer has been derivatised, it may be a different atom, for example a nitrogen atom.

Z is preferably a group of the formula —Y$^2$-L-Y$^3$, wherein Y$^2$ represents a single bond, —C(O)—, —C(O)NR$^{17}$— or —C(O)O—, Y$^3$ represents a single bond, —C(O)—, —C(O)NR$^{17}$—, —NR$^{17}$—C(O)—, —C(O)O—, —O—C(O)—, —NR$^{17}$— or —O—, L is a bridging group which is preferably a substituted or unsubstituted aliphatic group or a substituted or unsubstituted aromatic group, typically comprising up to 6 carbon atoms. More preferably, L is a C$_{2-4}$ alkylene group, especially an ethylene group. R$^{17}$ is —H, a substituted or unsubstituted aliphatic group, such as a C$_{1-4}$ alkyl, particularly a methyl group or a substituted or unsubstituted aromatic group, particularly a phenyl group. Most preferably, Z is a group of formula —CO—CH$_2$CH$_2$—CO—O—.

Protecting groups which can be represented by Q will be selected according to the nature of Z, and include amine and hydroxy protecting groups, preferably acid labile hydroxy protecting groups, and especially optionally substituted trityl groups, such as mono- and dimethoxytrityl groups.

Nucleosides and oligonucleotides which can be represented by Q are as described above, preferably ribonucleosides and deoxyribonucleoside, including abasic nucleosides. The nucleoside or oligonucleotide may be attached to the support via different positions known in the art. Preferably, the attachment is via the 5'- or 3'—, most preferably the 3'-position of a ribonucleoside or deoxyribonucleoside moiety.

Suitable optional substituents for aliphatic groups, aryl groups, aralkyl groups, heteroaryl groups, azaheteroaryl groups and heteroalicyclyl groups include aryl groups, halogenated aryl groups, alkyl groups, halogenated alkyl (e.g. trifluoromethyl and trichloromethyl), aliphatic ethers, aromatic ethers, benzyl, substituted benzyl, halogens, particularly chloro and fluoro groups, cyano, nitro, —S-(aliphatic or substituted aliphatic group), and —S-(aromatic or substituted aromatic).

Preferred compositions of matter are compounds of the formula:

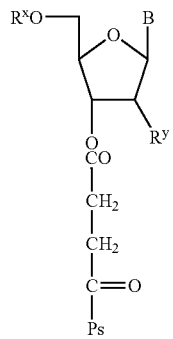

Wherein Ps is as described above, $R^x$ is an acid labile protecting group, preferably an optionally substituted trityl, especially a dimethoxytrityl, group, $R^y$ is H, F, allyl, OMe, $OCH_2CH_2OMe$, or hydroxy protected by a base labile or silyl-protecting group, and B is H, a protected adenine, guanine, or cytosine moiety or an optionally protected thymine, uracil or hypoxanthine moiety.

The compositions of matter according to the present invention can be prepared by applying methods known in the art for attaching cleavable linkers and nucleosides to polymeric supports to the polymers used in the process for preparing oligonucleotides according to the first aspect of the present invention.

The invention will now be described, without limitation, by the following examples.

EXAMPLE 1

Preparation of trityl-tetraethyleneglycoxystyrene

Stage 1

Tetraethyleneglycol (174 g, 0.9 mol) was placed in a 3 necked round bottom flask fitted with a thermometer and reflux condenser. Pyridine (11 cm³, 0.135 mol) was added to the mixture stirred. Triphenylmethylchloride (25 g, 0.09 mol) was dissolved in toluene (30 cm³) and this solution was added slowly to the mixture. The mixture was heated to 50° C. and the temperature maintained for 1 h.

The mixture was allowed to cool and toluene (200 cm³) was added to the flask. The solution was extracted with water (500 cm³). The aqueous phase was back extracted with toluene (2 × 100 cm³). The organic layers were combined and washed with water (2×100 cm³), dried over $MgSO_4$ and filtered. The toluene was removed by evaporation under reduced pressure to yield a pale yellow oil (yield 38.5 g, 98% based on trityl).

Stage 2

Mono(trityl)tetraethyleneglycol (30 g, 0.069 mol), 4-toluenesulfonyl chloride (14.4 g, 0.076 mol) and dry tetrahydrofuran (THF, 50 cm³) were placed in a 3 necked round bottom flask fitted with a thermometer and reflux condenser. The flask was placed in a dry-ice bath and the mixture allowed to cool to ~−20° C. A solution of KOH (25.2 g, 0.45 mol) in water (100 cm³) was added drop-wise over a period of 1 h whilst maintaining the temperature at <0° C. Following the addition the reaction mixture was stirred for 1 h whilst allowing the solution to warm to ambient.

The solution was extracted with diethylether (3×150 cm³). The ether layer was dried over $MgSO_4$, filtered and evaporated under reduced pressure. The solid was washed with MeOH and dried under vacuum (yield 34.3 g, 85%).

Stage 3

NaOMe (0.55 g, 10.2 mmol) was dissolved in the minimum amount of N,N-dimethylformamide (DMF) and added to 4-acetoxystyrene (1.3 cm³, 8.5 mmol) contained in a round bottom flask. This solution was stirred at ambient for 45 min then a solution of the tosyl derivative of mono(trityl)tetraethyleneglycol (5 g, 8.5 mmol) in DMF was added. The reaction was allowed to continue overnight at ambient.

The DMF was removed by evaporation under reduced pressure. The oil remaining was dissolved in isopropylacetate and extracted with water. The organic layers were combined, dried over $MgSO_4$ and filtered. The solvent was removed by evaporation under reduced pressure to leave a pale yellow oil that crystallised on standing (yield 3.5 g, 77%).

EXAMPLE 2

10 Litre Scale Preparation of trityl-tetraethyleneglycoxystyrene

Stage 1

Tetraethylene glycol (4188 g, 21.5 mol) was added under a nitrogen atmosphere to a 10l vessel equipped with a mechanical stirrer and stirred at 60 rpm. Pyridine (544 g, 6.9 mol) was added to the vessel and the mixture heated to 50° C. Triphenylmethyl chloride (1000 g, 3.6 mol) was dissolved in toluene (3000 ml) under $N_2$ atmosphere and added slowly to the glycol keeping the temperature below 60° C. The temperature was held at 50° C. for 2 hours and then cooled to room temperature. 2 l of toluene were added and the mixture extracted with 6 l of deionised water, the water phase extracted with 5 l of toluene. The combined organic extracts were washed with 2×4 l of Dl water, dried over 500 g sodium sulphate and solvent removed under reduced pressure to yield 1230 g (74% based on trityl) of a pale yellow oil, 94.3% purity (by NMR)

Stage 2

Mono(trityl)tetraethyleneglycol (1766.4 g, 3.8 mol) was added to a 10 l vessel together with 3 l THF and cooled under agitation to −12° C. p-Toluenesulphonyl chloride (945 g, 5 mol) was added to the glycol/THF mixture. A solution of KOH (880 g, 15.7 mol) in deionised water (3 l) was added to the solution over 1 hour keeping the temp below −5° C. After completion of the addition the vessel was warmed to 25° C. and held for 12 hours. The phases were separated and the lower aqueous layer washed with 2×2.5 L THF, the organic layers combined and solvent removed under reduced pressure. The orange/brown oil in 7.5 l isopropyl acetate was extracted with 10 l water and then 5×2 l water, dried over magnesium sulphate (500 g) and solvent removed to give 1837 g (78.0%) of the product as a viscous orange oil, purity 95.3% (by NMR).

Stage 3

Deionised water (1.5 l) and THF (2.1 l) were added to a 10 L vessel and agitation started at 100 rpm. The vessel was cooled down to −12° C. and potassium hydroxide (535 g, 9.5 mol) was added slowly. Acetoxystyrene (575 ml, 3.7 mol) in THF (1 l), was added to the vessel over about 30 minutes with cooling. The vessel was heated to 30° C. and held for 1 hr, then cooled to 20° C. The Stage 2 product (1800 g, 2.9 mol) in 1050 ml THF was added to reaction vessel over 15 mins, then the mixture heated at 60° C. for 40 hrs. The reaction was cooled, the phases separated and the organic layers washed with 2×2 l of 8M aqueous potassium hydroxide. The solvent was removed under reduced pressure and the residue dissolved in toluene (5 l), washed with 3×2 l deionised water, then 2×2 l 1M aqueous sodium hydroxide, and finally 2×3 l DI water. The organic layer was dried with sodium sulphate (500 g) and solvent removed under reduced pressure to yield 1471 g (75%) of the product as an orange oil, purity 79.7% by NMR.

EXAMPLE 3

Synthesis of Polymer and Subsequent Deprotection

Partially hydrolysed poly(vinyl alcohol) (Airvol 540, 34.9 g of 2.5 wt-% aqueous solution) and sodium chloride (31.2 g) were charged into a 2 l cylindrical baffled reactor containing deionised water (1181 ml) and equipped with a mechanical stirrer. A mixture of Stage 3 product (79.7%, 87.2 g), styrene (59.1 g), divinylbenzene (80%, 1.4 g) and lauroyl peroxide were charged to the reactor and agitated at 400 rpm. After 20 minutes the stirrer speed was reduced to 300 rpm and the reaction heated with a water bath to 80° C. over 50 minutes. After 16 h, the reaction mixture was cooled, transferred to a 50 μm filter cloth bag and washed with deionised water (5×1 l). The polymer beads were then washed with THF (4×1 l) and dichloromethane (DCM, 2×1 l) and stirred at room temperature under nitrogen in a 5 l flange flask/overhead stirrer with a mixture of dichloromethane (1800 ml), trifluoroacetic acid (128 g) and triethylsilane (51.5 g) for 4 hours. The product was then washed with dichloromethane (4×1 l) and hexane (5×1 l) before drying to constant weight in a vacuum oven, yielding 78 g of white polymer beads with a hydroxyl loading of 0.97 mmol/g.

EXAMPLE 4

Coupling of 5'-DMTrOABz-3'—Succinate with Polymer

Polymer prepared by the method of Example 3 (0.51 g, 0.357 mmol) was charged to a 50 ml round-bottomed flask equipped with a small magnetic follower. 5'-DMTrOABz-3'-succinate (1.28 g, 4 eq) and hydroxybenzotriazole (HOBT, 0.29 g, 6 eq) were dissolved in N-methylpyrrolidinone (NMP, ca. 5 ml) and diisopropylcarbodiimide (DIC, 0.19 g, 4.2 eq) was added to this solution. Diisopropylethylamine (0.19 g, 4.1 eq) was added to this solution ca. two minutes after the DIC had been added. This whole solution was swirled then quickly added to the flask containing the resin. Glassware and equipment contaminated with DIC was detoxified in a bath of 2 M sodium hydroxide.

The flask was stoppered and the mixture was stirred slowly for ca. 70 hours. The red/brown mixture was transferred to a sinter funnel and filtered under suction and the resin was washed with NMP (3×~20 ml). Any remaining free hydroxyl groups were capped by adding a solution of acetic anhydride (0.29 g, 8 eq) and dimethylaminopyridine (DMAP, 0.02 g, 0.5 eq) in NMP (~30 ml) and holding for 1 hour, bubbling nitrogen gas up through the resin bed to provide agitation. The reagents were discharged and the resin was washed with DMF (5×10 ml), DCM (5×10 ml) and was finally collapsed with diethyl ether (3×20 ml). The resin was blown dry with a stream of nitrogen and dried in a vacuum oven at room temperature overnight. The spent reagent solution was treated with NaOH solution for detoxification.

Weight of product: 0.739 g

EXAMPLE 5

Preparation of 5'—HOABz-3'-succinate-polymer

5'-DMTrOABz-3-succinate-polymer prepared in Example 4 (0.739 g) was charged to a solid phase reactor comprising a jacketed sintered reactor adapted for operation under a nitrogen atmosphere fitted with a septum inlet and a Rotaflo tap. Both the nitrogen inlet and outlet were fitted with in-line drying tubes filled with self-indicating $P_2O_5$. The 5'-DMTrO-ABz-3-succinate-polymer was washed with DCM (~10 ml). The reactor jacket was cooled to 0° C. with a fluid circulator. 3% v/v dichloroacetic acid (DCA) in DCM (60 ml) was passed through the resin bed under suction. A red colour developed on the beads but did not diffuse rapidly into the solution. The beads also floated on the top of the solution. Once all of the acid solution had passed through the reactor, the resin was washed with DMF (5×~5 ml) and then DCM (5×5 ml). Washing the resin was achieved by passing a flow of nitrogen gas up through the resin bed and adding the solvent, then replacing the nitrogen supply with a vacuum to drain the resin.

With nitrogen gas flowing up through the resin bed, 3% v/v DCA solution in DCM (15 ml) was charged to the reactor. A deep red colour developed immediately. After 1 minute the nitrogen flow was swapped for a vacuum and the acid solution was discharged. A further 30 ml of 3% acid solution was passed through the resin under suction. A third 15 ml aliquot of 3% acid solution was held with the resin for 1 minute with nitrogen bubbling before being discharged under suction. The resin was washed with DMF (5×~5 ml) and DCM (5×~5 ml).

A further "hold-flush-hold" treatment was carried out as described in the preceding paragraph and after the resin had been washed it was collapsed by washing with diethyl ether (3×~10 ml).

HPLC analysis of filtrates did not show the presence of N-benzoyl adenine, as would be expected if depurination of the A nucleoside had occurred.

EXAMPLE 6

Synthesis of GTACA Oligonucleotide

This was achieved using phosphoramidite chemistry using the following coupling and detritylation conditions. Conventional 5'-dimethoxytrityideoxyribonucleoside-3'-betacyanoethyloxy-N,N-diisopropylphosphoramidites were employed.

Coupling

For all "dry" steps in coupling reactions (i.e. from pre-coupling washes up to and including sulfurization) the DMF used was commercial anhydrous DMF (ex Aldrich), which was dried overnight over 4 Å molecular sieves in ca. 100 ml batches as required. This gave DMF with a moisture content of 5-50 ppm (Karl-Fischer), c.f. ~150 ppm as initially supplied. Discharging of solutions was achieved in these steps by applying a positive pressure of $N_2$ gas to the top of the reactor via the Rotaflo tap and applying suction from below the sinter. The support used initially in this series of reactions was 5'—HOABz-3'-succinate-polymer prepared in Example 5 above.

Details are given for the first coupling and detritylation in the series (dCbz amidite+5'-HOABz-3'-succinate-polymer). Subsequent couplings and detritylations were executed in an identical manner using the same number of equivalents of the corresponding phosphoramidite reagent (dAbz, dT and dGibu amidites).

5'—HOABz-3'-succinate-polymer (0.320 mmol) was charged to the solid-phase reactor, which was fitted with a septum inlet and a Rotaflo tap and adapted for operation under a nitrogen atmosphere. Both the nitrogen inlet and outlet were fitted with in-line drying tubes filled with self-indicating $P_2O_5$. The resin was washed with dry DMF (3×~5 ml) and dry DCM (2×~5 ml). The amidite (0.67 g, 0.8 mmol, 2.5 eq) was dried azeotropically with MeCN (2×10 ml) and dissolved in dry DCM (~3 ml). Saccharin methyl imidazole salt, prepared by the methods of International Patent Application WO03/004512 (SMI, 0.21 g, 0.8 mmol, 2.5 eq) was charged to an oven-dried vial fitted with a septum and dissolved in dry DMF (~0.5 ml) and dry DCM (~2.5 ml). The amidite and SMI solutions were then charged to the pre-swollen resin, in that order, via the septum inlet.

After a two hour hold with gentle bubbling of the mixture with $N_2$ gas, dry methanol (~2 ml) was added. After ca. 5 minutes the solution was discharged from the reactor and the resin was washed with dry DMF (3×~5 ml) and dry pyridine (2×~5 ml). The spent reagent solution was analysed by HPLC to estimate the amount of active amidite remaining at the end of the reaction.

A solution of xanthane hydride (0.12 g, 0.8 mmol, 2.5 eq) in dry pyridine (~4 ml) was charged to the resin and this was held, with gentle $N_2$ bubbling, for one hour after which the solution was discharged. The top was removed from the reactor and the resin was washed with bench DMF (5×~5 ml) and DCM (5×~5 ml) and then with Cap A solution (5:3:2 MeCN:Py:NMI, 2×~5 ml). Cap A solution (2.5 ml) and Cap B solution (4:1 MeCN:$Ac_2O$, 2.5 ml) were then charged to the reactor and the mixture was held for one hour.

The spent capping solution was discharged and the resin was then washed with DMF (5×~5 ml) and DCM (5×~5 ml) and finally with diethyl ether (3×~5 ml). The resin was then left overnight before detritylation.

Detritylation

Prior to detritylation the reactor jacket was cooled to 0° C. and the resin was washed/pre-swollen with DCM. 3% (v/v) DCA in DCM ("acid solution") was used to detritylate the resin. For each detritylation cycle, the volume of acid solution used was based on 167 ml per mmol of DMT assumed to be attached to the resin.

Acid solution (12 ml) was held with the resin for 1 minute with agitation by nitrogen gas from below the sinter. The bright red solution was discharged by suction and a further 25 ml of acid solution was passed through the resin bed. A third 12 ml aliquot of acid solution was held with the resin for 1 minute before being discharged. The resin was washed with DMF (5×~5 ml) and with DCM (5×~5 ml).

This cycle of acid treatment/washing was repeated once more. After the final DCM wash the resin was collapsed by washing with diethyl ether (3×~5 ml).

The average coupling yield over the 4 coupling steps was calculated by trityl analysis as 97.5%.

The invention claimed is:

1. In a process for the preparation of an oligonucleotide by assembly of the oligonucleotide attached to a solid support, the improvement wherein the solid support is prepared by polymerisation of a monomer which comprises a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with a poly-aryl methane protecting group.

2. A process according to claim 1, wherein the solid support is prepared by a polymerisation of a monomer of the following formula

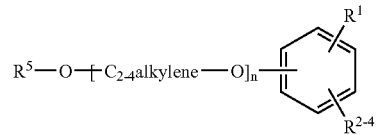

wherein $R^1$ is an optionally substituted ethylene group;

$R^{2-4}$ are independently hydrogen, hydrocarbyl, halogen, or hydrocarbyloxy;

$R^5$ is an optionally substituted trityl group; and n is 2 to 10.

3. A process according to claim 2, wherein $R^1$ is para to the group of formula $R^5$—O—[$C_{2-4}$alkylene-O]—, $R^1$ is an unsubstituted ethylene group, $R^{2-4}$ are each H, the $C_{2-4}$ alkylene group is —$CH_2CH_2$— and n is 4.

4. A process according to claim 1, wherein the support is crosslinked.

5. A process according to claim 1, wherein the oligonucleotide is assembled by phosphoramidite chemistry.

6. A process according to claim 1, wherein the oligonucleotide is attached to the solid support via a cleavable linker.

7. A process according to claim 6, wherein the cleavable linker is a succinyl, oxalyl or trityl linker.

8. A process according to claim 1, further comprising cleaving the oligonucleotide from the solid support.

9. A process according to claim 8, wherein the oligonucleotide is deprotected prior to, concomitant with, or after, cleavage from the solid support.

10. A composition of matter having the formula:

Ps-Z-Q wherein

Ps represents a polymer obtained by polymerisation of a monomer which comprises a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and is protected with a poly-aryl methane protecting group;

Z represents a single bond or a cleavable linker; and

Q represents H, a nucleoside or an oligonucleotide, provided that Q is not H when Z represents a single bond.

11. A composition of matter according to claim 10, wherein Z is a group of the formula —$Y^2$-L-$Y^3$, wherein $Y^2$ represents a single bond, —C(O)—, —C(O)$NR^{17}$— or —C(O)O—, $Y^3$ represents a single bond, —C(O)—, —C(O)$NR^{17}$—, —$NR^{17}$—C(O)—, —C(O)O—, —O—C(O)—, —$NR^{17}$— or —O—, $R^{17}$ is —H, a substituted or unsubstituted aliphatic group or a substituted or unsubstituted aromatic group and L is a bridging group.

12. A composition of matter according to claim 11, wherein L is a $C_{2-4}$ alkylene group.

13. A composition of matter according to claim 12 of the formula:

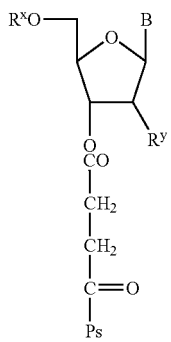

wherein $R^x$ is an acid labile protecting group, $R^y$ is H, F, allyl, OMe, OCH$_2$CH$_2$OMe, or hydroxy protected by a base labile or silyl-protecting group, and B is H, a protected adenine, guanine, or cytosine moiety or an optionally protected thymine, uracil or hypoxanthine moiety.

14. The process of claim 1 wherein the protecting group is a trityl group, a dimethoxytrityl group or a 2-chlorotrityl group.

15. The composition of matter of claim 10 wherein the protecting group is a trityl group, a dimethoxytrityl group or a 2-chlorotrityl group.

* * * * *